(12) United States Patent
Bohmann et al.

(10) Patent No.: US 11,865,111 B2
(45) Date of Patent: Jan. 9, 2024

(54) ANTIVIRAL DRUGS TARGETING THE N-TERMINAL DOMAIN (NTD) OF THE CORONAVIRUS SPIKE RECEPTOR BINDING DOMAIN (RBD)

(71) Applicants: Southwest Research Institute, San Antonio, TX (US); The Government of The United States, as represented by The Secretary of the Army, Fort Detrick, MD (US); The Henry M. Jackson Foundation for the Advancement of Military Medicine, Inc., Bethesda, MD (US)

(72) Inventors: Jonathan A. Bohmann, San Antonio, TX (US); Nadean M. Gutierrez, Devine, TX (US); Joseph A. McDonough, Helotes, TX (US); Robert Francis Campbell, Edgemere, MD (US); Michael Gordon Joyce, Silver Spring, MD (US); Rekha Panchal, Fort Detrick, MD (US); Rajeshwer Sankhala, Bethesda, MD (US); Allen Duplantier, Stafford, VA (US)

(73) Assignees: Southwest Research Institute, San Antonio, TX (US); The Henry M. Jackson Foundation for the Advancement of Military Medicine, Inc., Bethesda, MD (US); The Government of the United States, as Represented by the Secretary of the Army, Fort Detrick, MD (US)

( * ) Notice: Subject to any disclaimer, the term of this patent is extended or adjusted under 35 U.S.C. 154(b) by 0 days.

(21) Appl. No.: 17/819,178

(22) Filed: Aug. 11, 2022

(65) Prior Publication Data

US 2023/0074535 A1 Mar. 9, 2023

Related U.S. Application Data

(60) Provisional application No. 63/260,342, filed on Aug. 17, 2021.

(51) Int. Cl.
| | | |
|---|---|---|
| *A61P 31/02* | (2006.01) |
| *A61K 31/4184* | (2006.01) |
| *A61K 31/445* | (2006.01) |
| *A61K 31/551* | (2006.01) |
| *A61K 31/4468* | (2006.01) |
| *C07D 295/112* | (2006.01) |
| *C07D 295/096* | (2006.01) |
| *C07D 409/04* | (2006.01) |
| *C07D 223/04* | (2006.01) |

(52) U.S. Cl.
CPC .............................. *A61K 31/445* (2013.01)

(58) Field of Classification Search
CPC ... A61P 31/12; A61K 31/4184; A61K 31/445; A61K 31/551; A61K 31/4468; C07D 295/112; C07D 295/096; C07D 409/04; C07D 223/04

See application file for complete search history.

(56) References Cited

U.S. PATENT DOCUMENTS

2021/0079008 A1 3/2021 Davis et al.

OTHER PUBLICATIONS

Gelemanovic et al., Identification of 37 Heterogeneous Drug Candidates for Treatment of COVID-19 via a Rational Transcriptomics-Based Drug REpurposing Approach, Pharmaceuticals, vol. 14, No. 2, 87 (Year: 2021).*
Pinto et al., Screening of World Approved Drugs Against Highly Dynamical Spike Glycoprotein SARS-CoV-2 using CaverDock and Machine Learning, ChemRxiv, 2020 pp. 1-19 (Year: 2020).*
Invitation to Pay Additional Fees from corresponding PCT Appln. No. PCT/US2022/074840, dated Feb. 14, 2023.
"SID 400226951", PubChem, downloaded Feb. 14, 2023, concise explanation of relevancy can be found in the Invitation to Pay Additional Fees submitted herewith.
"SID 85862052", PubChem, downloaded Feb. 14, 2023, concise explanation of relevancy can be found in the Invitation to Pay Additional Fees submitted herewith.
"SID 400226951", PubChem, Modify date Feb. 17, 2021, downloaded Mar. 24, 2023, concise explanation of relevancy can be found in the International Search Report and Written Opinion submitted herewith herewith.
International Search Report and Written Opinion from corresponding PCT Appln. No. PCT/US2022/074840, dated Apr. 13, 2023.

* cited by examiner

*Primary Examiner* — Brenda L Coleman
(74) *Attorney, Agent, or Firm* — Grossman, Tucker, Perreault & Pfleger, PLLC

(57) ABSTRACT

Antiviral drugs targeting the N-terminal domain (NTD) of the spike receptor binding domain (RBD) and methods of treating a subject suffering from coronavirus.

6 Claims, 16 Drawing Sheets
(16 of 16 Drawing Sheet(s) Filed in Color)

ANTIVIRAL DRUGS TARGETING THE N-TERMINAL DOMAIN (NTD) OF THE CORONAVIRUS SPIKE RECEPTOR BINDING DOMAIN (RBD)

STATEMENT REGARDING FEDERALLY SPONSORED RESEARCH OR DEVELOPMENT

This invention was made with government support under W81XWH-18-2-0040 awarded by the United States Army Medical Research and Development Command. The government has certain rights in the invention.

FIELD

The present invention is directed at antiviral drugs targeting the N-terminal domain (NTD) of the spike receptor binding domain (RBD) and methods of treating a subject suffering from coronavirus.

BACKGROUND

Coronavirus disease has led to a global pandemic. Coronavirus disease-19 (COVID-19) was reportedly first identified in Wuhan (Hubei province, China) at the end of 2019 and later, the International Committee on Taxonomy of Viruses (ITVC) named it SARS-CoV-2 due to its similarity to SARS-CoV.

SUMMARY

A method for treatment of SARS-COV-1, SARS-CoV-2 (Covid-19) and MERS-CoV, and variants within each, in a mammalian subject in need thereof, comprising administering to the subject an effective amount of the following benzimidazole compounds:

wherein, X can be —$CH_2$— or C=O, and R can be —$OCH_3$ or —$NHCH_3$;
or a pharmaceutically acceptable salt thereof, optionally in a pharmaceutically acceptable carrier.

A method for treatment of SARS-COV-1, SARS-CoV-2 (Covid-19) and MERS-CoV, and variants within each, in a mammalian subject in need thereof, comprising administering to the subject an effective amount of the following piperdine compounds:

wherein $R_1$ or $R_2$ can be a hydroxy and the other is H, methoxy (—$OCH_3$) or ethoxy (—$OCH_2CH_3$) and $R_3$ and $R_4$ are independently H, F, Cl, $CF_3$ or —$OCH_3$; or a pharmaceutically acceptable salt thereof, optionally in a pharmaceutically acceptable carrier.

A method for treatment of SARS-COV-1, SARS-CoV-2 (Covid-19) and MERS-CoV, and variants within each, in a mammalian subject in need thereof, comprising administering to the subject an effective amount of 3-[4-[3-(3,4,5-trimethoxybenzoyl)oxypropyl]-1,4-diazepan-1-yl]propyl 3,4,5-trimethoxybenzoate or a pharmaceutically acceptable salt thereof, optionally in a pharmaceutically acceptable carrier.

A method for treatment of SARS-COV-1, SARS-CoV-2 (Covid-19) and MERS-CoV, and variants within each, in a mammalian subject in need thereof, comprising administering to the subject an effective amount of N-(2,2,2-trifluoroethyl)-9-(4-(4-(4'-(trifluoromethyl)-[1,1'-biphenyl]-2-carboxamido)piperidin-1-yl)butyl)-9H-fluorene-9-carboxamide, or a pharmaceutically acceptable salt thereof, optionally in a pharmaceutically acceptable carrier.

An antiviral drug for treatment of SARS-COV-1, SARS-CoV-2 (Covid-19) and MERS-CoV, and variants within each, in a mammalian subject in need thereof, comprising methyl 3-(((3-(5-(1H-benzo[d]imidazol-2-yl)thiophen-3-yl)benzyl)amino)methyl)benzoate.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION

Figure 1:
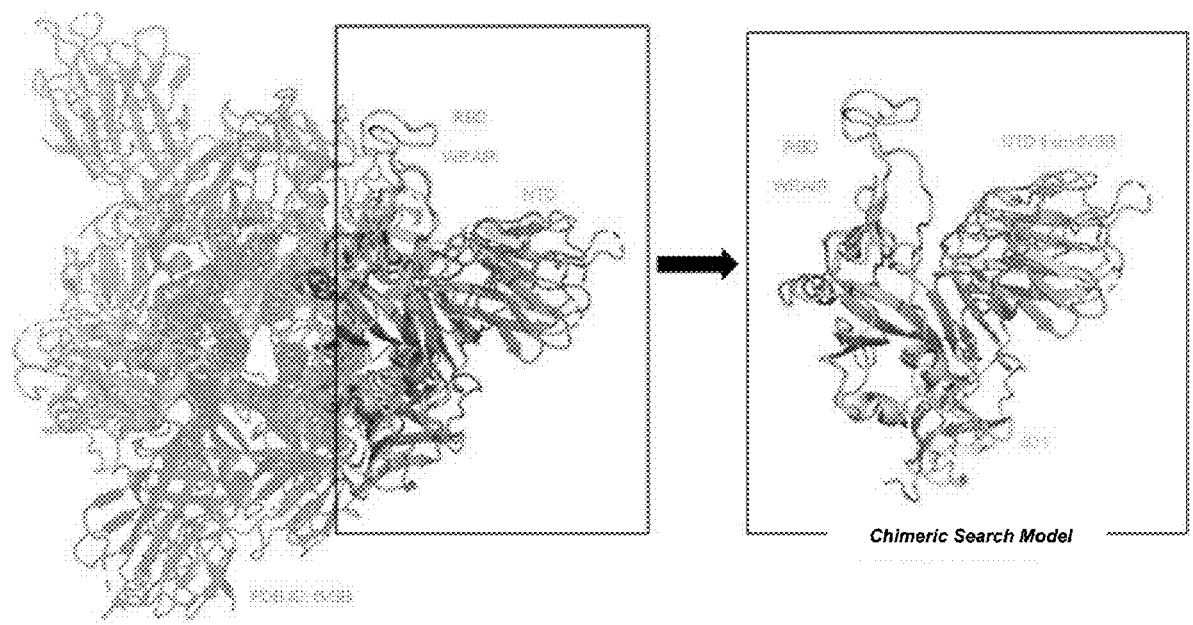
FIG. 1. SARS-CoV-2 Spike glycoprotein RBD-NTD-SD1 chimera model. The RBD-NTD-SD1 model was created by overlaying a high resolution RBD structure with chain B of the SARS-CoV-2 S trimer (PDB ID: 6VSB), and extracting the SD1 from chain B, the NTD from chain C. The relative locations of the domains to each other, allowed definition of cavities that could be targeted for in-silico inhibitor search.

Compositions and methods of treating a subject suffering from SARS-COV-1, SARS-CoV-2 (Covid-19) and MERS-CoV, and variants within each, are provided, which targets the N-terminal domain (NTD) of the spike receptor binding domain (RBD). Reference to a subject, individual, host or patient herein are interchangeable and refer to any mammalian subject for which diagnosis, treatment is therapy is desired, particularly humans. Treatment may be any treatment of a disease in a mammal and includes preventing the disease from occurring, inhibiting the disease, arresting its development, or relieving or causing regression of the disease.

In Vitro Screening Protocol

As an initial matter, screening of the drugs identified herein for antiviral activity was conducted. Specifically, primary screening of small molecules was performed by testing the compounds at a single final concentration of 10 µM in two independent replicate plates. Compounds that showed >50% infection inhibition and <20% loss in cell number in both replicated plates were considered as hits. To determine potency and selectivity index of identified hits, compounds were tested in 8-point dose response with a 3-fold step dilution at concentration ranging from 30-0.01 µM and four replicates. N-hydroxy cytidine (NHC), an antiviral with known anti SARS-CoV-2 activity, was used as a reference inhibitor.

All infections with virulent strains were performed in a BSL-3 laboratory in accordance with CDC and US Army safety regulations. To identify small molecule inhibitors of SARS-CoV-2, VeroE6 cells (ATCC CRL-1586) were seeded at a density of 4000 cells/well in a 384 well imaging plates (Aurora Microplates, ABE2-31101A). Next day cells were pre-treated with the compound for two hours and then infected with SARS-CoV-2 (USA-WA1/2020) at a multiplicity of infection (MOI) of 0.01. After 32 hours following infection, cells were fixed in 10% formalin. To detect the viral antigen, immunofluorescence staining was performed wherein formalin fixed cells were washed three times with Phosphate buffered saline (PBS) and then incubated at room temperature (RT) with 50 µl of a combination cell permeabilization and blocking buffer (3% BSA, 0.1% Triton X-100 in PBS). After 1 hour, blocking buffer was replaced with 50 µl primary antibody solution (SARS-CoV/SARS-CoV-2 Nucleocapsid Rabbit Mab, Sino Biological, Cat 40143-R001) diluted 1:1000 in PBS and allowed to bind for 1 hour at RT. After two washes with 50 µl PBS, cells were stained for 30 minutes with 1:500 dilution of Alexa 488 anti-rabbit IgG (Invitrogen A11031). After 30 minutes, cells were washed three times with PBS. In the final step, PBS was replaced with 50 µl per well of 1:10000 Hoechst nuclear dye (Invitrogen H3570) and 5 mg/ml HCS Cellmask Deep Red (Invitrogen H32721), a cytoplasmic stain, all diluted with PBS.

To quantitate viral infection, images were acquired using a Perkin Elmer Opera quad-excitation confocal microscope (model 5025) using a 10× air objective. The nuclei, viral nucleoprotein, and cytoplasm were detected using the 405, 488, and 640 nm channels, respectively. Virus-positive cells were identified by presence of 488 excitation signal within the boundary denoted by cytoplasmic mask. Intensity cutoffs were determined by the intensity of background fluorescence in uninfected control wells, and were normalized for each separate experiment. The robustness of the assay was determined by calculating the Z' value on a per plate basis (Ji-Hu Zhang J, Thomas D. Y. Chung and Kevin R. Oldenburg, *A Simple Statistical Parameter for Use in Evaluation and Validation of High Throughput Screening Assays*, J. of Biomolecular Screening, 4:67, 1999) and using the following formula:

$$Z' = (1 - (3 \times STDEV \text{ of Signal}_{max}(\text{neutral/infection only control}) + 3 \times STDEV \text{ Signal}_{min}(\text{inhibitor/no infection control})) / ABS(\text{mean Signal}_{max} - \text{mean of Signal}_{min}))$$

Plates that have Z'>0.5 were considered for data analysis. To determine percent of viral infection inhibition and cytotoxicity in presence of compound, the Acapella generated cell data is imported to Spotfire (visual analysis statistical software, Perkin Elmer Inc., MA). Compounds that exhibited greater than 50% inhibition of SARS-CoV-2 infection relative to infected control (infected and DMSO treated) wells and those that did not reduce the number of cells more than 20% relative to the infected control were considered as "Hits". The hit compounds were then selected for dose-response assays.

To determine the potency ($EC_{50}$, $EC_{90}$), cytotoxicity ($CC_{50}$) and selectivity index (SI) of the compounds, dose response curve analysis was performed using GeneData software applying Levenberg-Marquardt algorithm (LMA) for curve-fitting strategy. Fitting strategy is considered acceptable if $R^2 > 0.8$.

Antiviral Potential for Targeting the SARS-CoV-2

Multiple coronaviruses infect humans causing significant illness and disease, highlighted by the recent zoonotic emergence of SARS-CoV-2. Coronaviruses have a typical Spike glycoprotein molecule located on the virion surface. The SARS-CoV-2 Spike glycoprotein is a Type I fusion glycoprotein made up of three intercalating monomers to form a metastable trimer. Each Spike monomer is cleaved into S1 and S2 by furin enzymatic activity. The S1 region contains an N-terminal domain (NTD), and a receptor-binding domain (RBD). The process of human infection and viral-cell entry is initiated by binding of the RBD to the human Angiotensin-converting enzyme 2 (ACE2) receptor. This then enables a transition of the metastable spike from a prefusion form, allowing "release" of the fusion peptide and structural rearrangements that enable viral-cell fusion and cell entry. The SARS-CoV-2 RBD adopts two main conformations in relation to the Spike, referred to as the "up" conformation (where the RBD ACE2 binding site is accessible) and the "down" conformation (where the ACE2 binding site is inaccessible). The coronavirus spike glycoprotein is essential for SARS-CoV-2.

The intercalated nature of the three spike glycoprotein monomers means that the RBD from one chain is side-by-side with the NTD from another chain. This domain organization was contemplated to allow for flexibility and hinging of the RBD receptor site from an inaccessible "down" location to a fully accessible "up" conformation. The antiviral targeting of the Spike RBD involved two rationales, (i) blocking the ACE2 binding site, and (ii) hindering the transition of the RBD into an "up" conformation and thus preventing accessibility of the ACE2 binding site. The ACE2 binding site on the RBD contains hydrophobic patches while there is also a subtle conformational transition of the flexible 476-486 loop upon ACE2 binding. This site has been targeted by peptide-based inhibitors (utilizing short stretches of residues from the ACE2 protein such as 22-44) that interrupt the ACE2-RBD interaction [PMID: 32917884] and have antiviral activity [PMID: 33310780]. More recent analysis of the SARS-CoV-2 Spike structure has identified a "Free fatty acid binding pocket" in the locked structure of SARS-CoV-2 spike protein (PDB ID: 6ZB4) [PMID: 32958580], largely involving the RBD but in essence stabilizing the "closed" conformation of the Spike.

It was determined herein that a high resolution RBD structure at 1.95 Angstrom allowed complete mapping of the RBD (residues 332-526), side chain rotamers, including the flexible 476-486 loop region. This molecule was then docked onto the trimeric spike (PDB ID: 6VSB). See FIG. 1. The locations of the RBD and a proximal adjacent NTD and SD1 relative to each other were extracted from the overlaid molecules, to create an RBD-NTD-SD1 model. This model was made up of the high resolution RBD structure (residues 321-526, including water molecules and glycans) and the NTD-SD1 structure (residues 27-294, 321-331, 527-591) from the EM model. This hybrid model allowed identification of compounds adjacent to RBD residues 355, 396, 428, 462, 464 and NTD residues 197, 201, 231, 331.

Figure 2A:
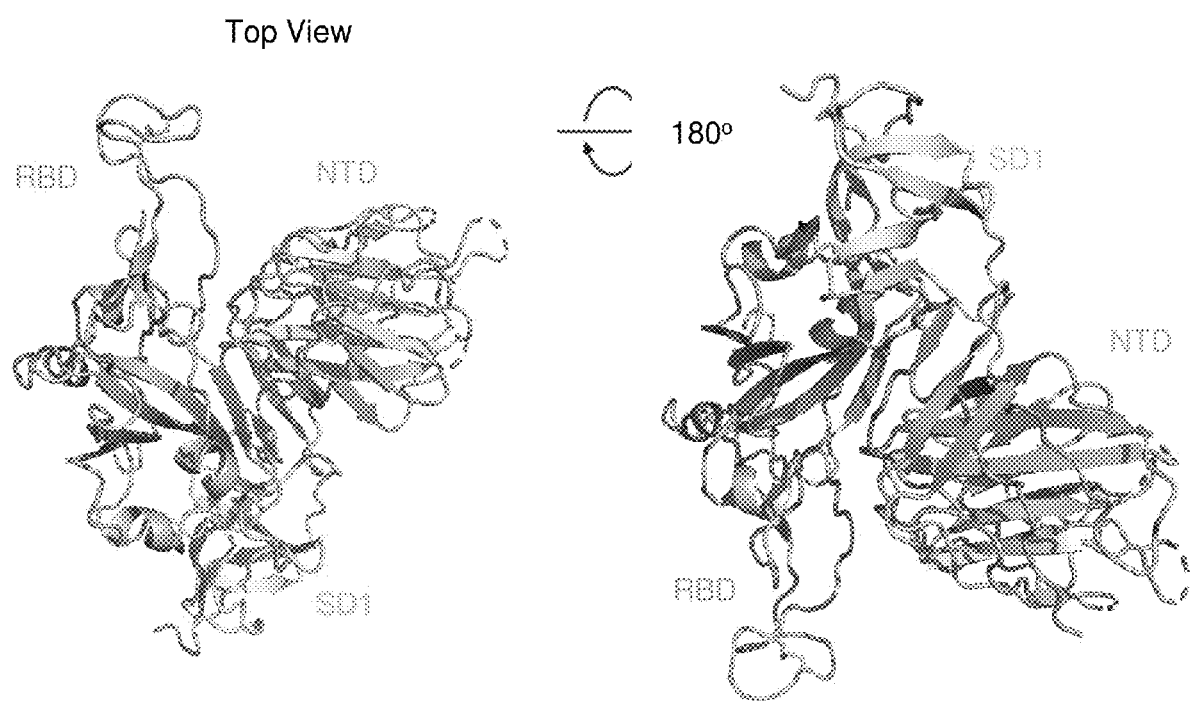
FIG. 2A shown the RBD-NTD-SD1 model used to search for binding inhibitors is shown in ribbon representation in two views, (left) a view looking down from above the Spike glycoprotein, and (right) rotated 180°, view internal to the Spike glycoprotein.
Figure 2B:
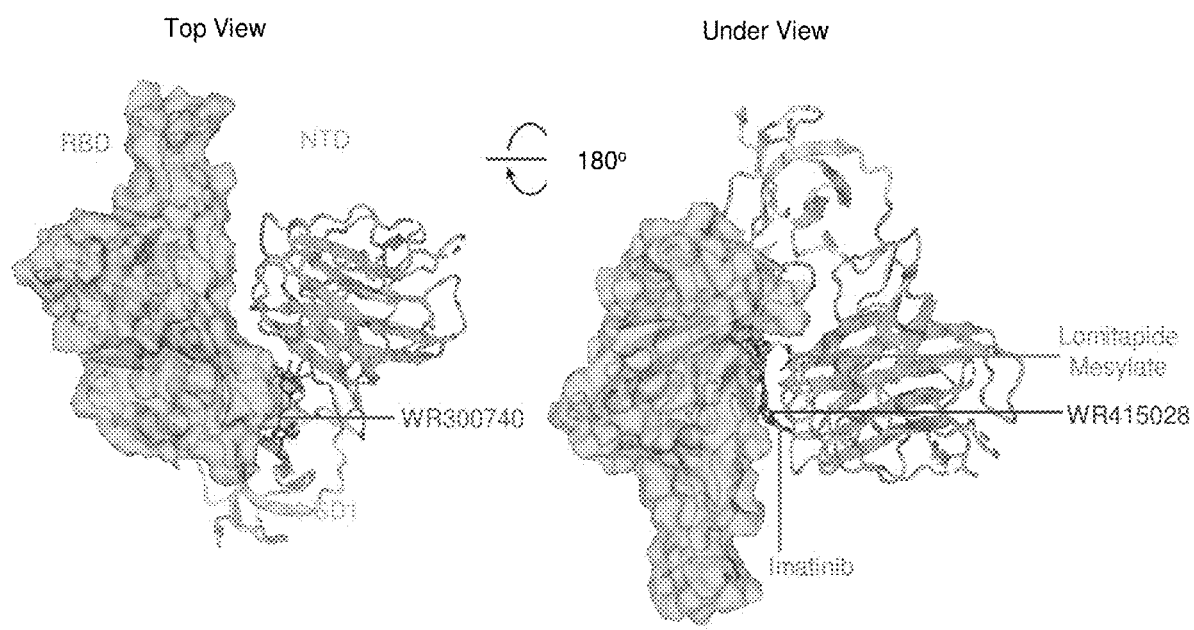
FIG. 2B shows the RBD-NTD-SD1 model with surface representation, and four compounds identified from the in-silico search.
Figure 2C:
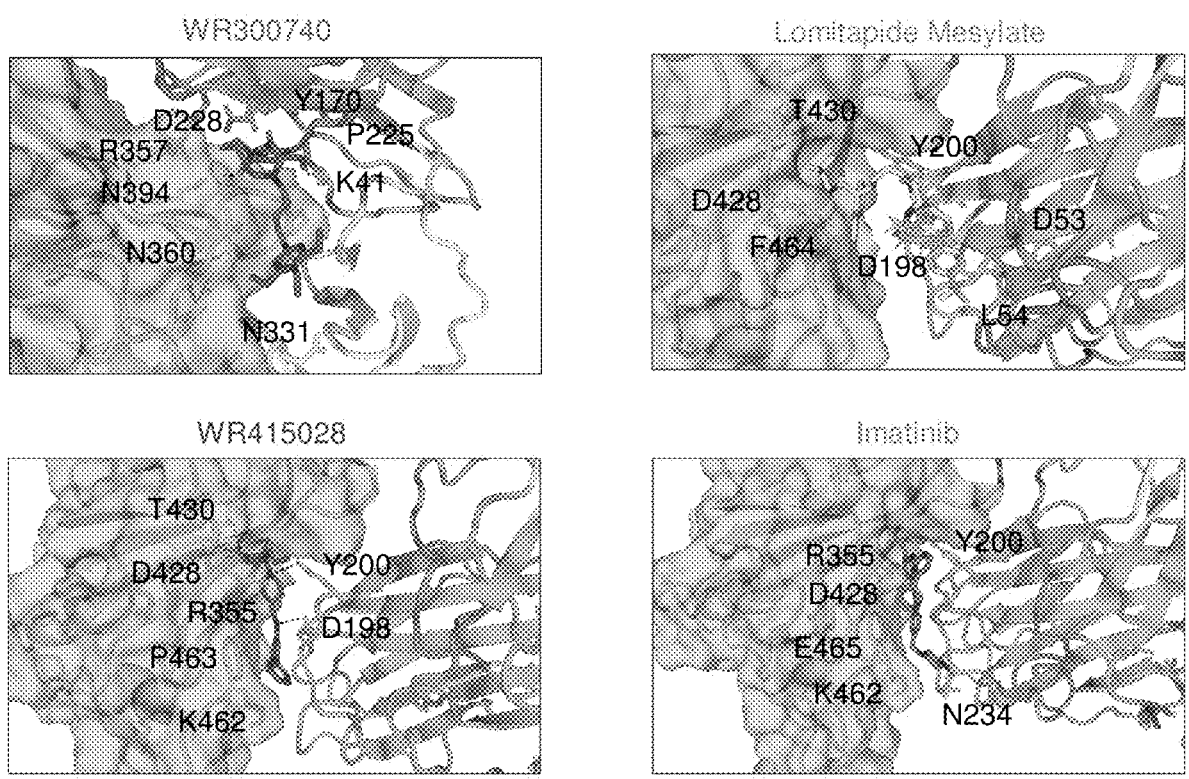
FIG. 2C provides a zoom-in view of the putative binding sites for four compounds, with close contact residues shown in stick representation and labelled.

See FIGS. 2A, 2B and 2C which shows the SARS-CoV-2 Spike glycoprotein RBD-NTD-SD-1 model and putative small molecule binding sites. These binding pockets are constructed from discontinuous regions of both the RBD and NTD. WR415028 is Compound 4 herein, 1-(3-ethoxy-4-hydroxybenzyl)-N-(3'-fluoro-[1,1'-biphenyl]-3-yl)piperidine-4-carboxamide. WR300740 is reference to Dilazep or 3-(4-{3-[(3,4,5-Trimethoxyphenyl)carbonyloxy]propyl}-1,4-diazepan-1-yl)propyl 3,4,5-trimethoxybenzoate. Lomitapide mesylate is reference to N-(2,2,2-Trifluoroethyl)-9-[4-[4-[[[4'-(trifluoromethyl)[1,1'-biphenyl]-2-yl]carbonyl]amino]-1-piperidinyl]butyl]-9H-fluorene-9-carboxamide methanesulfonate. Imatinib is reference to 4-[(4-methylpiperazin-1-yl)methyl]-N-(4-methyl-3-{[4-(pyridin-3-yl)pyrimidin-2-yl]amino}phenyl)benzamide.

Accordingly, the present invention is directed at antiviral drugs targeting and methods of treating a subject suffering from SARS-COV-1, SARS-CoV-2 (Covid-19) and MERS-CoV, and variants within each, in a mammalian subject. The method comprises administering to the subject the compounds identified herein, or a pharmaceutically acceptable salt thereof, optionally in a pharmaceutically acceptable carrier. The pharmaceutically acceptable carrier may comprise a dosage form suitable for oral administration, such as in a solution or suspension. The dosage form may be in a solid dosage form such as a tablet, capsule or gel cap. The pharmaceutically acceptable carrier may also include a dosage suitable for intravenous delivery.

The administration is contemplated to provide a reduction in the subject's viral load (which can be evaluated via PCR), an improvement in one or more of the subjects viral infection symptoms (e.g. fever, decreased oxygen saturation, shortness of breath, difficulty breathing, fatigue, muscle aches, body aches, chest pain or pressure, headache, loss of taste, loss of smell, sore throat, congestion, nausea, vomiting, diarrhea, confusion, cough or rash) and/or clinical status. Clinical status may be evaluated utilizing the WHO Ordinal Scale for Clinical Improvement.

In a first embodiment the antiviral drug targeting the N-terminal domain (NTD) of the spike receptor binding domain (RBD) of SARS-COV-1, SARS-CoV-2 (Covid-19) and MERS-CoV, and variants within each, comprises benzimidazoles or pharmaceutically acceptable salts therefore identified in Formula I below:

In the above, X can be —CH$_2$— or C=O, and R can be —OCH$_3$ or —NHCH$_3$.

Figure 3:
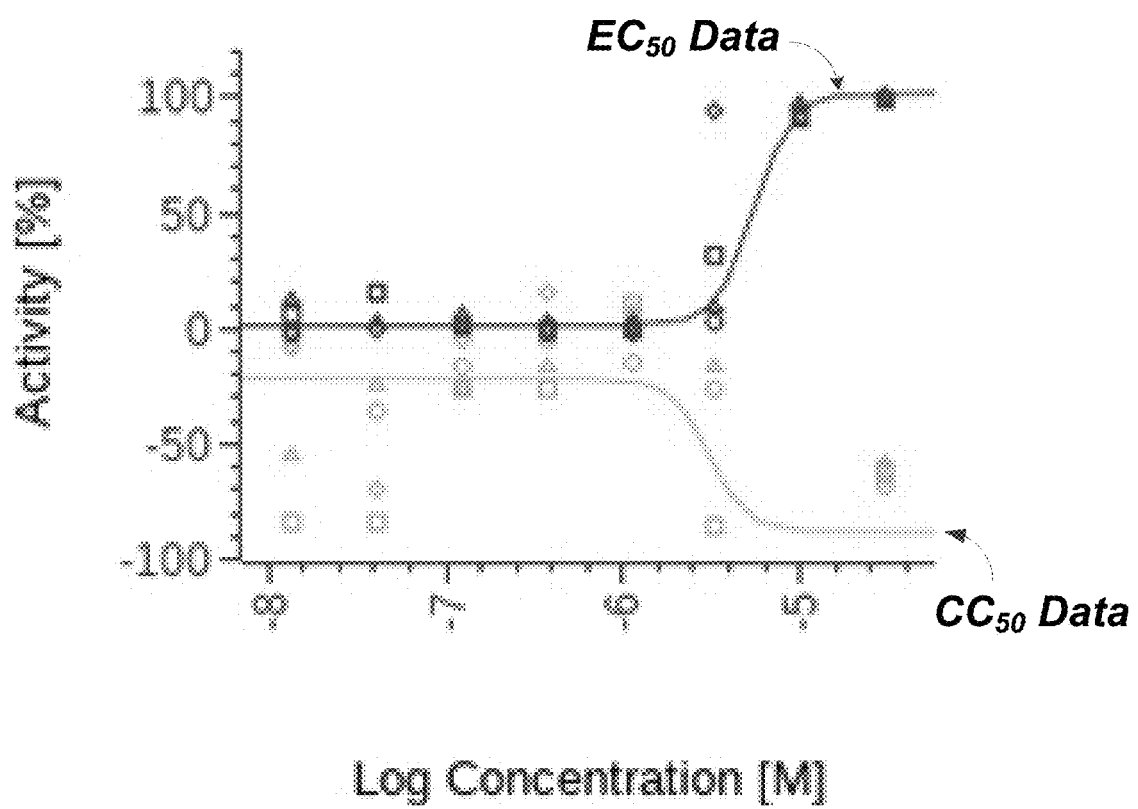
FIG. 3 is the dose response curve for Compound 1, methyl 3-(((3-(5-(1H-benzo[d]imidazol-2-yl)thiophen-3-yl)benzyl)amino)methyl)benzoate.
Figure 4:
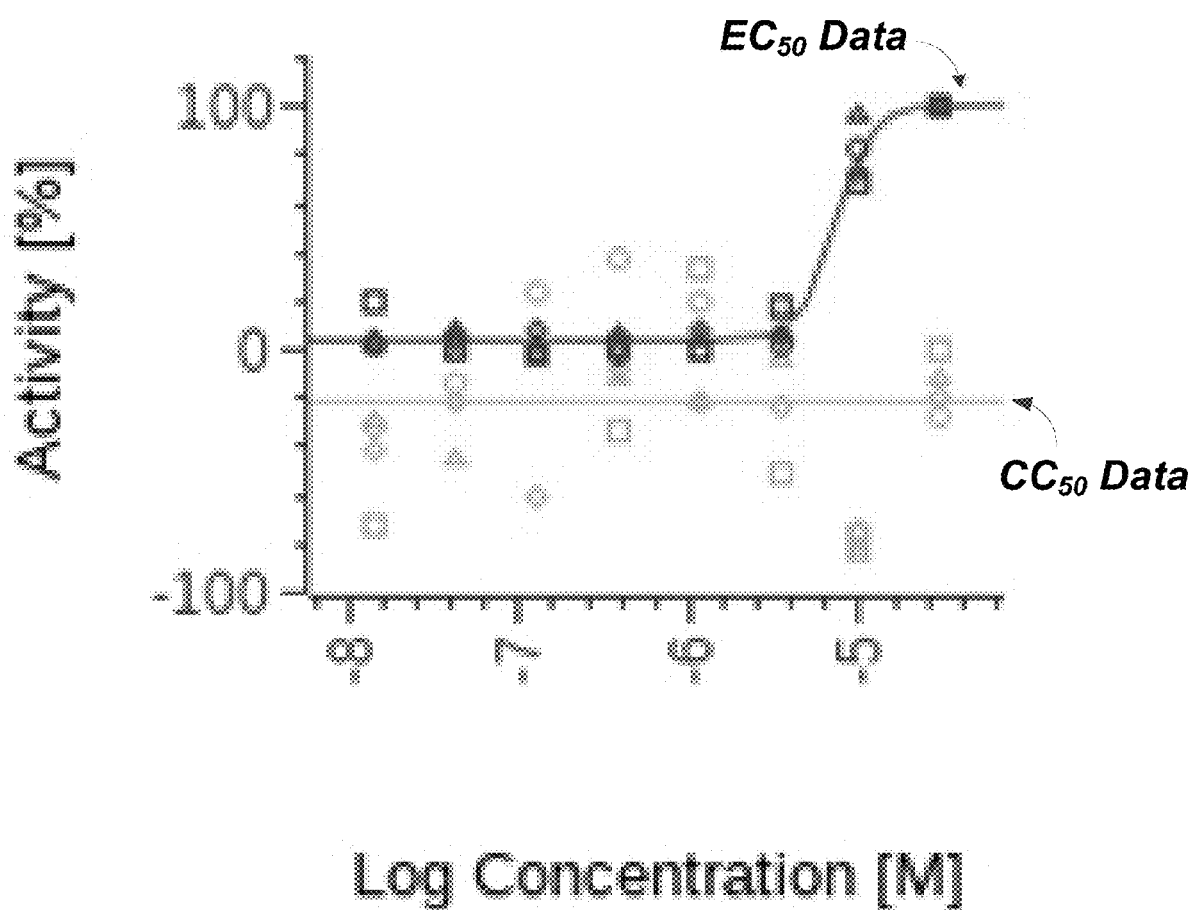
FIG. 4 is the dose response curve for Compound 2, 3-(((3-(5-(1H-benzo[d]imidazol-2-yl)thiophen-3-yl)benzyl)amino)methyl)-N-methylbenzamide
Figure 5:
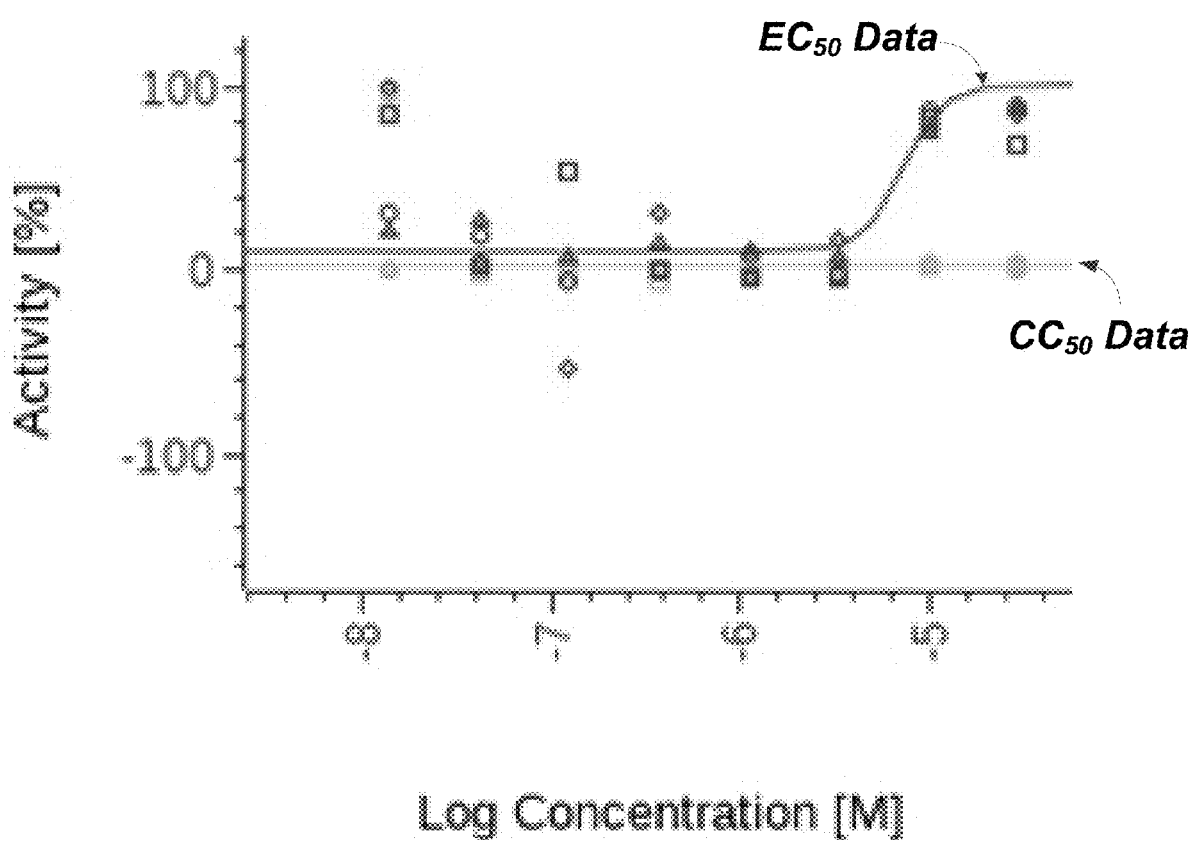
FIG. 5 is the dose response curve for Compound 3, methyl 3-((3-(5-(1H-benzo[d]imidazol-2-yl)thiophen-3-yl)benzamido)methyl)benzoate.
Figure 6:
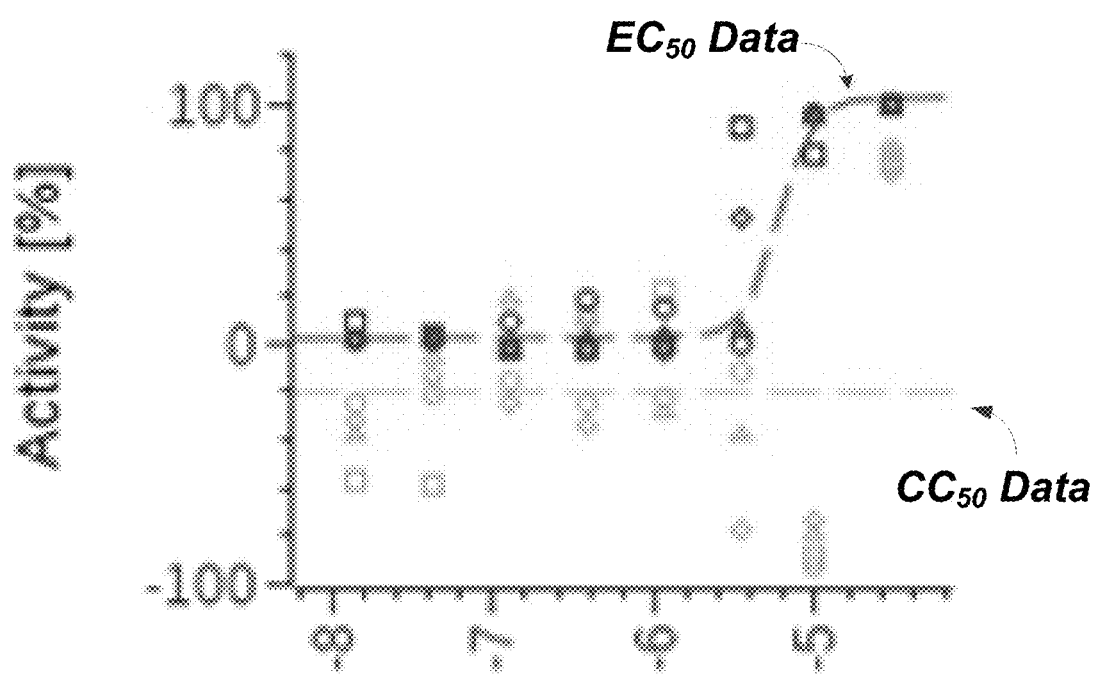
FIG. 6 is the is the dose response curve for Compound 4, 1-(3-ethoxy-4-hydroxybenzyl)-N-(3'-fluoro-[1,1'-biphenyl]-3-yl)piperidine-4-carboxamide.
Figure 7:
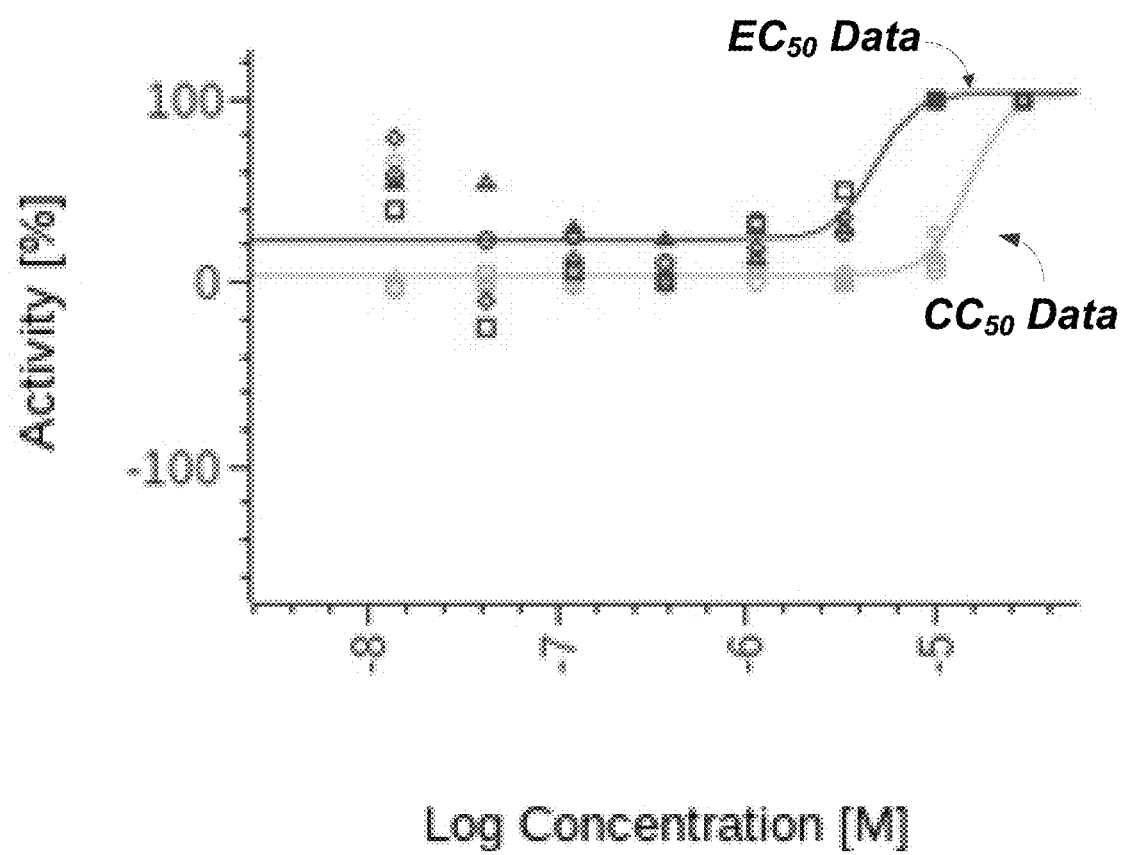
FIG. 7 is the dose response curve for Compound 5, 1-(3-ethoxy-4-hydroxybenzyl)-N-(3'-(trifluoromethyl)-[1,1'-biphenyl]-3-yl)piperidine-4-carboxamide.
Figure 8:
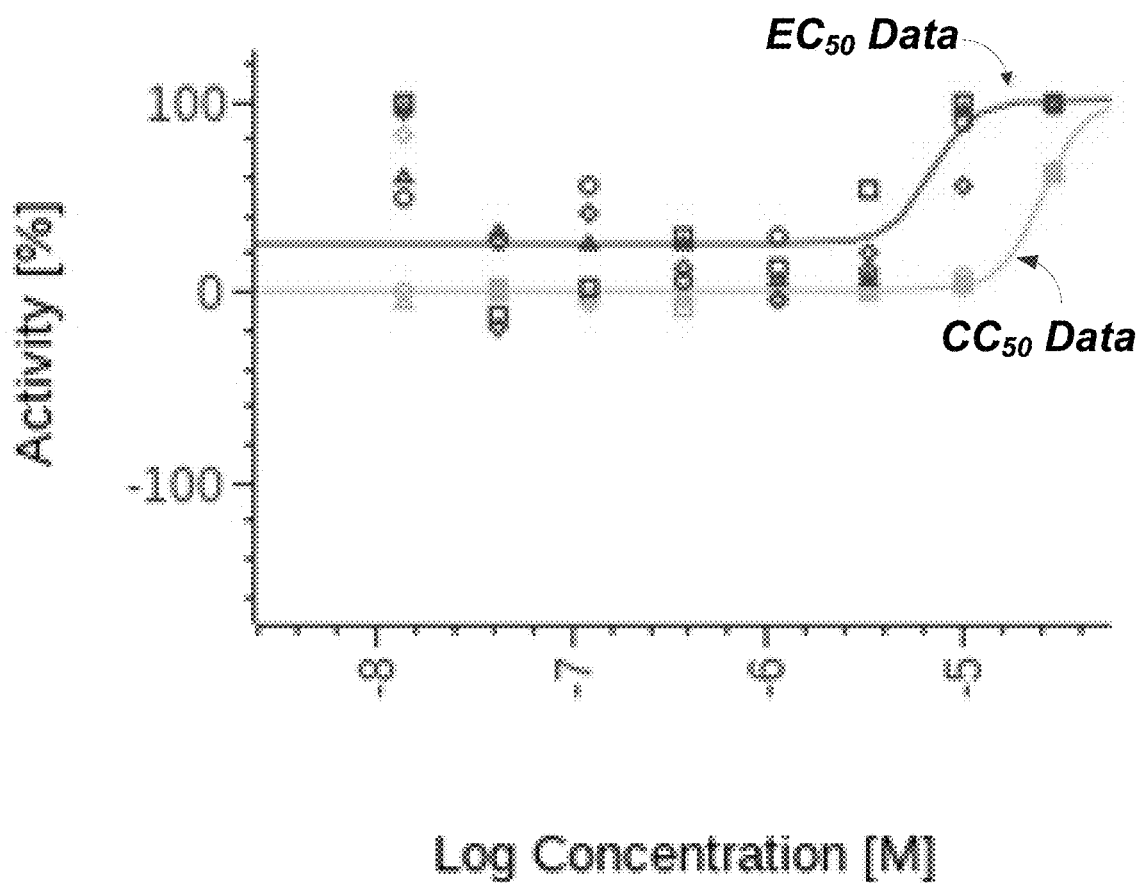
FIG. 8 is the dose response curve for Compound 6, 1-(3-ethoxy-4-hydroxybenzyl)-N-(3'-methoxy-[1,1'-biphenyl]-3-yl)piperidine-4-carboxamide.
Figure 9:
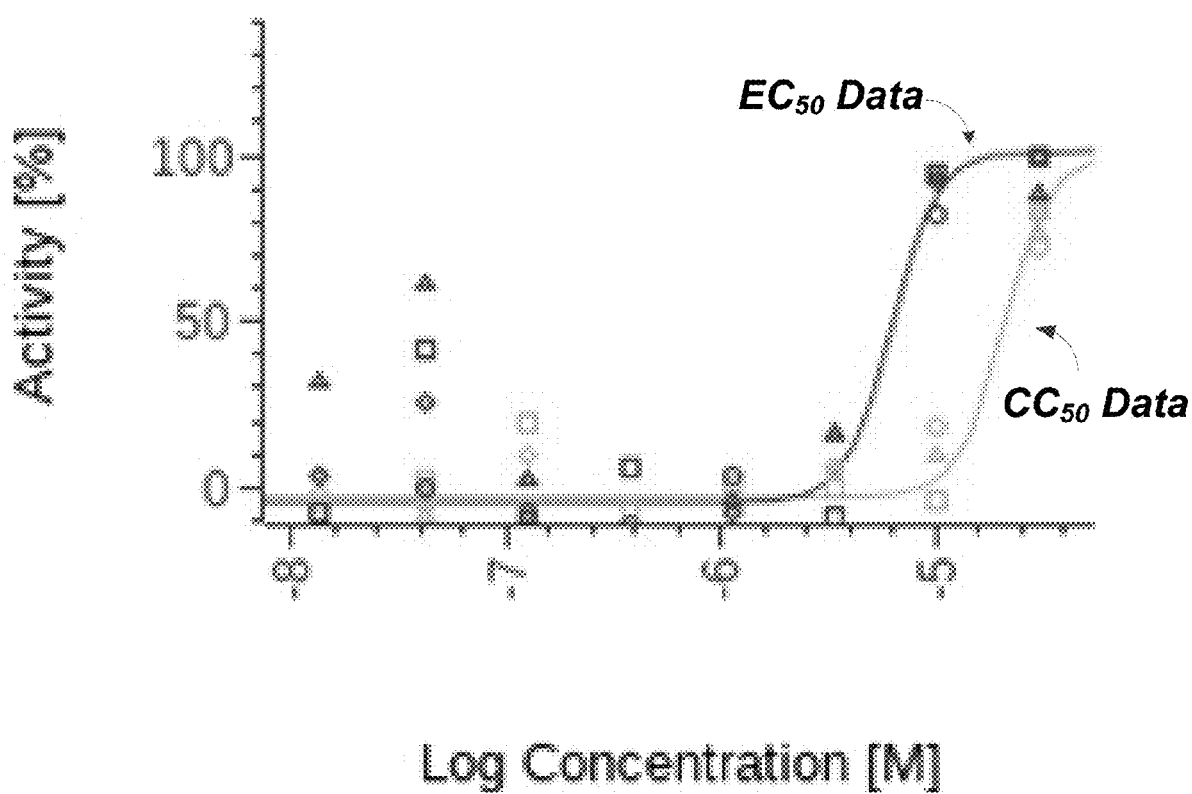
FIG. 9 is the dose response curve for Compound 7, N-(3'-chloro-[1,1'-biphenyl]-3-yl)-1-(4-hydroxybenzyl)piperidine-4-carboxamide.
Figure 10:
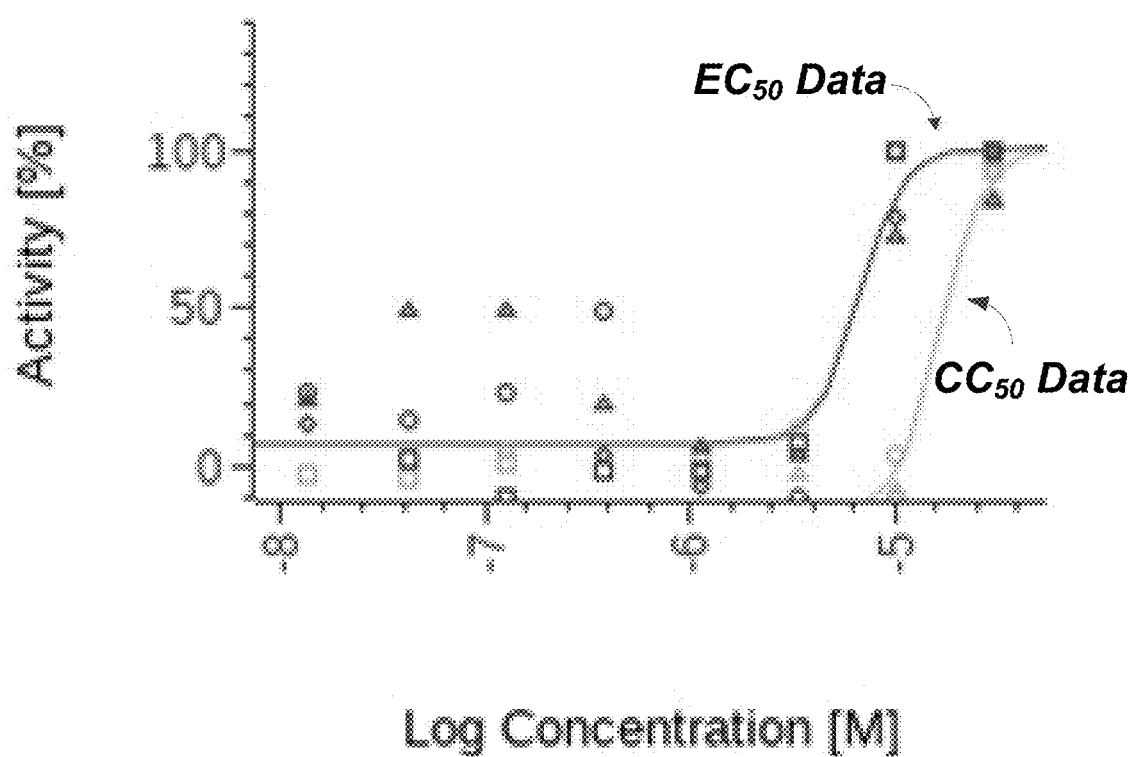
FIG. 10 is the dose response curve for Compound 8, N-(3'-chloro-[1,1'-biphenyl]-3-yl)-1-(3-hydroxy-4-methoxybenzyl)piperidine-4-carboxamide.
Figure 11:
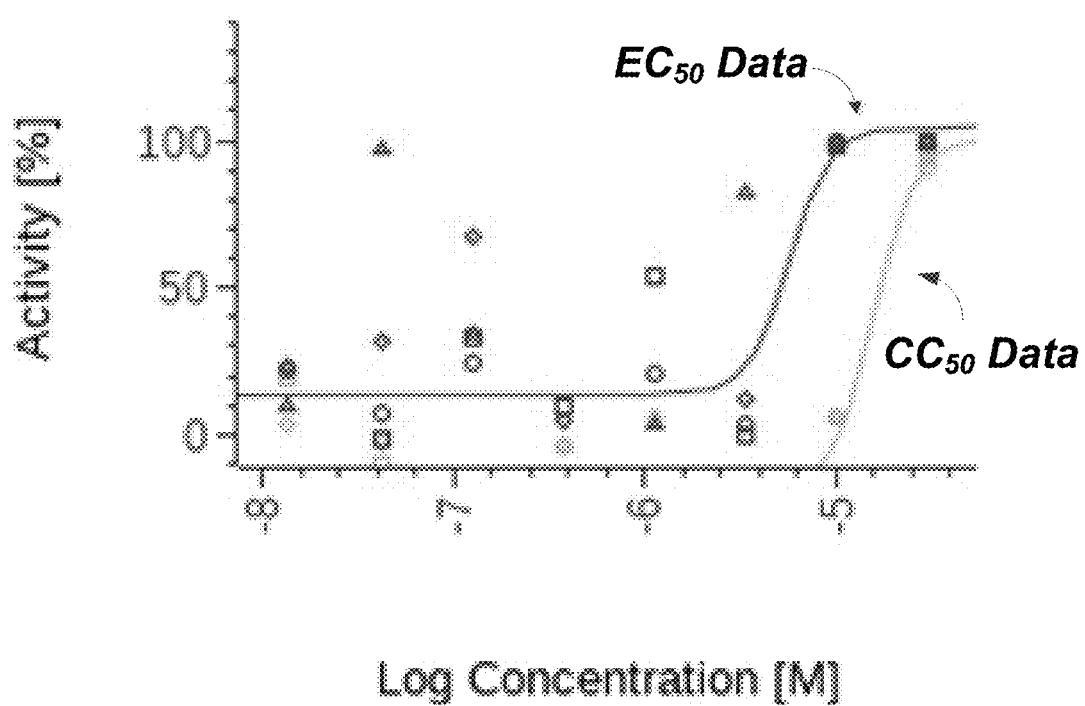
FIG. 11 is the dose response curve for Compound 9, N-(3'-chloro-[1,1'-biphenyl]-3-yl)-1-(3-ethoxy-4-hydroxybenzyl)piperidine-4-carboxamide.
Figure 12:
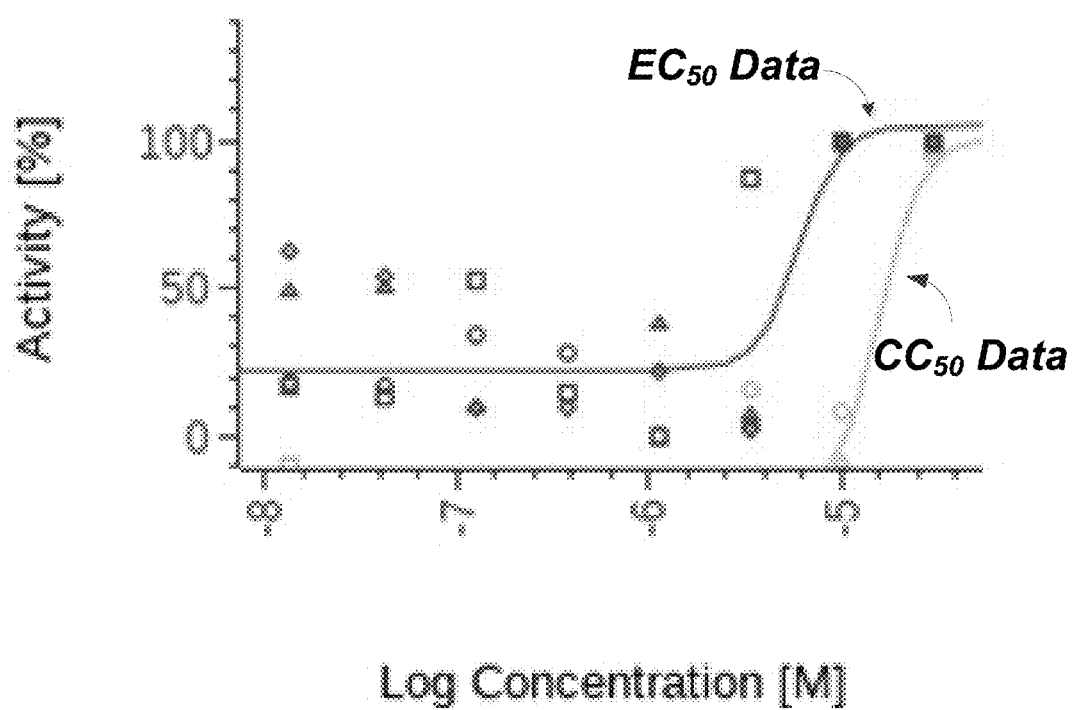
FIG. 12 is the dose response curve for Compound 10, N-(4'-chloro-[1,1'-biphenyl]-3-yl)-1-(3-ethoxy-4-hydroxybenzyl)piperidine-4-carboxamide.

Preferably, the antiviral drugs in Formula I herein comprise:

1. Compound 1: methyl 3-(((3-(5-(1H-benzo[d]imidazol-2-yl)thiophen-3-yl)benzyl)amino)methyl)benzoate, which has the following general structure:

2. Compound 2: 3-(((3-(5-(1H-benzo[d]imidazol-2-yl)thiophen-3-yl)benzyl)amino)methyl)-N-methylbenzamide, which has the following general structure:

3. Compound 3: methyl 3-((3-(5-(1H-benzo[d]imidazol-2-yl)thiophen-3-yl)benzamido)methyl)benzoate, which has the following general structure:

Table 1 below provides data on potency ($EC_{50}$, $EC_{90}$), cytotoxicity ($CC_{50}$) and SI (selectivity index=$CC_{50}/EC_{50}$) for the above referenced compounds against the SARS-CoV-2 strain. $EC_{50}$ is reference to the dose that provides a half-maximal response. $EC_{90}$ is reference to the dose that provides a 90% maximal response. $CC_{50}$ is the concentration required for reduction of cell viability by 50%. The dose response curves for Compounds 1-3 are provided in FIGS. 3-5, respectively.

TABLE 1

| Compound | $EC_{50}$ (μM) | $EC_{90}$ (μM) | $CC_{50}$ (μM) | SI |
|---|---|---|---|---|
| 1 | 5.66 | 9.50 | >30.0 | >5.30 |
| 2 | 7.43 | 13.10 | >30.0 | >4.04 |
| 3 | 7.50 | 12.64 | >30.0 | >4.00 |

In a second embodiment the antiviral drug targeting the N-terminal domain (NTD) of the spike receptor binding domain (RBD) of SARS-COV-1, SARS-CoV-2 (Covid-19) and MERS-CoV, and variants within each, comprises piperdines or pharmaceutically acceptable salts therefore identified in Formula 2 below:

In the above, $R_1$ or $R_2$ can be a hydroxy and the other is H, methoxy (—$OCH_3$) or ethoxy (—$OCH_2CH_3$) and $R_3$ and $R_4$ are independently H, F, Cl, $CF_3$ or —$OCH_3$.

Preferably, the antiviral drugs in Formula 2 herein comprise:

4. Compound 4: 1-(3-ethoxy-4-hydroxybenzyl)-N-(3'-fluoro-[1,1'-biphenyl]-3-yl)piperidine-4-carboxamide, which has the following general structure:

5. Compound 5: 1-(3-ethoxy-4-hydroxybenzyl)-N-(3'-(trifluoromethyl)-[1,1'-biphenyl]-3-yl)piperidine-4-carboxamide, which has the following general structure:

6. Compound 6: 1-(3-ethoxy-4-hydroxybenzyl)-N-(3'-methoxy-[1,1'-biphenyl]-3-yl)piperidine-4-carboxamide, which has the following general structure:

7. Compound 7: N-(3'-chloro-[1,1'-biphenyl]-3-yl)-1-(4-hydroxybenzyl)piperidine-4-carboxamide, which has the following general structure:

8. Compound 8: N-(3'-chloro-[1,1'-biphenyl]-3-yl)-1-(3-hydroxy-4-methoxybenzyl)piperidine-4-carboxamide, which has the following general structure:

9. Compound 9: N-(3'-chloro-[1,1'-biphenyl]-3-yl)-1-(3-ethoxy-4-hydroxybenzyl)piperidine-4-carboxamide, which has the following general structure:

10. Compound 10: N-(4'-chloro-[1,1'-biphenyl]-3-yl)-1-(3-ethoxy-4-hydroxybenzyl)piperidine-4-carboxamide, which has the following general structure:

Table 2 below provides data on potency ($EC_{50}$, $EC_{90}$), cytotoxicity ($CC_{50}$) and SI (selectivity index=$CC_{50}/EC_{50}$) for the above referenced compounds against the SARS-CoV-2 strain. The dose response curves for Compounds 4-10 are provided in FIGS. 6-12, respectively.

| Compound | $EC_{50}$ (μM) | $EC_{90}$ (μM) | $CC_{50}$ (μM) | SI |
|---|---|---|---|---|
| 4 | 6.10 | 10.10 | >30.0 | >4.92 |
| 5 | 4.91 | 7.47 | 15.6 | 3.20 |
| 6 | 7.16 | 11.45 | 26.30 | 3.70 |

| Compound | EC$_{50}$ (µM) | EC$_{90}$ (µM) | CC$_{50}$ (µM) | SI |
|---|---|---|---|---|
| 7 | 6.40 | 11.00 | 21.00 | 3.36 |
| 8 | 6.90 | 11.70 | 17.00 | 2.48 |
| 9 | 5.80 | 8.90 | 16.00 | 2.80 |
| 10 | 6.20 | 9.10 | 16.00 | 2.65 |

Figure 13:
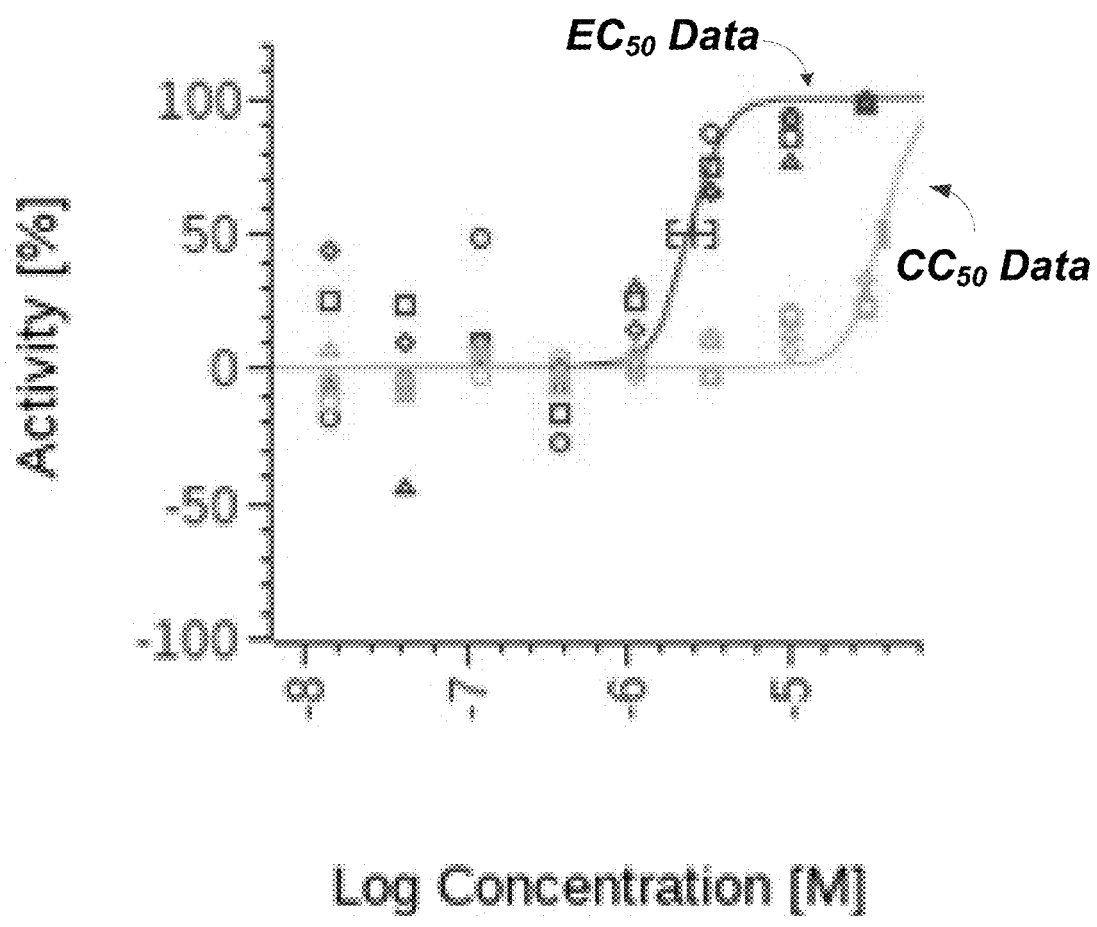
FIG. 13 is the dose response curve for Compound 11, dilazep.

In a third embodiment the antiviral drug which targets the N-terminal domain (NTD) of the spike receptor binding domain (RBD) of SARS-COV-1, SARS-CoV-2 (Covid-19) and MERS-CoV, and variants within each, comprises Formula 3, dilazep, otherwise known as 3-[4-[3-(3,4,5-trimethoxybenzoyl)oxypropyl]-1,4-diazepan-1-yl]propyl 3,4,5-trimethoxybenzoate, or a pharmaceutically acceptable salt thereof, optionally in a pharmaceutically acceptable carrier. Dilazep has the following general structure:

Dilazep indicated an EC$_{50}$ value of 3.89 uM+/−2.1, an EC$_{90}$ value of 19.8 uM, a CC$_{50}$ value of >30.0 uM and a SI of >7.7, against the SARS-CoV-2 strain. The dose response curve appears in FIG. 13.

Figure 14:
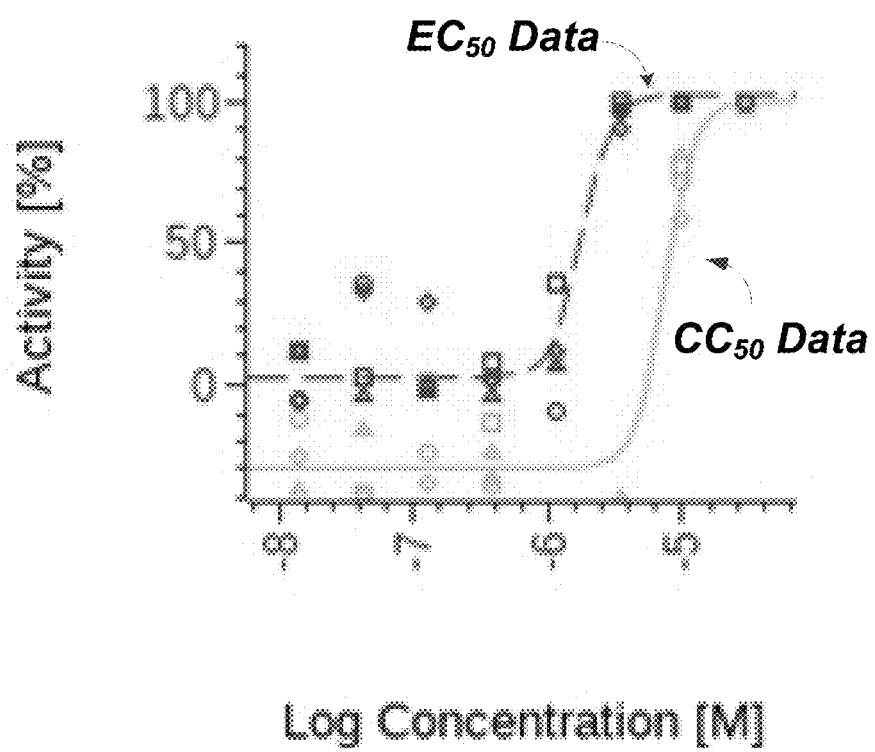
FIG. 14 is the dose response curve for N-(2,2,2-trifluoroethyl)-9-(4-(4-(4'-(trifluoromethyl)-[1,1'-biphenyl]-2-carboxamido)piperidin-1-yl)butyl)-9H-fluorene-9-carboxamide.

In a fourth embodiment, the antiviral drug which targets the N-terminal domain (NTD) of the spike receptor binding domain (RBD) of SARS-COV-1, SARS-CoV-2 (Covid-19) and MERS-CoV, and variants within each, comprises N-(2,2,2-trifluoroethyl)-9-(4-(4-(4'-(trifluoromethyl)-[1,1'-biphenyl]-2-carboxamido)piperidin-1-yl)butyl)-9H-fluorene-9-carboxamide, having the following general structure:

N-(2,2,2-trifluoroethyl)-9-(4-(4-(4'-(trifluoromethyl)-[1,1'-biphenyl]-2-carboxamido)piperidin-1-yl)butyl)-9H-fluorene-9-carboxamide indicated an EC50 value of 1.61, an EC90 value of 2.83 uM, a CC50 value of 9.56 uM and a SI of 5.92, against the SARS-CoV-2 strain. The dose response curve is provided in FIG. 14.

Those of skill in the art will recognize that the present invention may appear in a variety of forms other than the specific preferred embodiments described and contemplated herein.

What is claimed is:

1. A method for treatment of SARS-COV-1, SARS-CoV-2 (Covid-19) and MERS-CoV, and variants within each, in a mammalian subject in need thereof, comprising administering to the subject an effective amount of the following benzimidazole compounds:

wherein, X can be —CH$_2$— or C=O, and R can be —OCH$_3$ or —NHCH$_3$, or a pharmaceutically acceptable salt thereof, optionally in a pharmaceutically acceptable carrier.

2. The method of claim 1 wherein said benzimidazole compound comprises methyl 3-(((3-(5-(1H-benzo[d]imidazol-2-yl)thiophen-3-yl)benzyl)amino)methyl)benzoate.

3. The method of claim 1 wherein said benzimidazole compound comprises 3-(((3-(5-(1H-benzo[d]imidazol-2-yl)thiophen-3-yl)benzyl)amino)methyl)-N-methylbenzamide.

4. The method of claim 1 wherein said benzimidazole compound comprises methyl 3-((3-(5-(1H-benzo[d]imidazol-2-yl)thiophen-3-yl)benzamido)methyl)benzoate.

5. An antiviral drug for treatment of SARS-COV-1, SARS-CoV-2 (Covid-19) and MERS-CoV, and variants within each, in a mammalian subject in need thereof, comprising methyl 3-(((3-(5-(1H-benzo [d]imidazol-2-yl)thiophen-3-yl)benzyl)amino)methyl)benzoate.

6. A method for treatment of SARS-COV-1, SARS-CoV-2 (Covid-19) and MERS-CoV, and variants within each, in a mammalian subject in need thereof, comprising administering to the subject an effective amount of the following piperdine compounds selected from the group consisting of:
1-(3-ethoxy-4-hydroxybenzyl)-N-(3'-fluoro-[1,1'-biphenyl]-3-yl)piperidine-4-carboxamide;

1-(3-ethoxy-4-hydroxybenzyl)-N-(3'-(trifluoromethyl)-[1,1'-biphenyl]-3-yl)piperidine-4-carboxamide;
1-(3-ethoxy-4-hydroxybenzyl)-N-(3'-methoxy-[1,1'-biphenyl]-3-yl)piperidine-4-carboxamide;
N-(3'-chloro-[1,1'-biphenyl]-3-yl)-1-(3-hydroxy-4-methoxybenzyl)piperidine-4-carboxamide;
N-(3'-chloro-[1,1'-biphenyl]-3-yl)-1-(3-ethoxy-4-hydroxybenzyl)piperidine-4-carboxamide; or
N-(4'-chloro-[1,1'-biphenyl]-3-yl)-1-(3-ethoxy-4-hydroxybenzyl)piperidine-4-carboxamide.

\* \* \* \* \*